United States Patent [19]

Fernandez et al.

[11] Patent Number: 5,315,043

[45] Date of Patent: May 24, 1994

[54] AROMATIC NUCLEOPHILIC FLUORINATION

[75] Inventors: Richard E. Fernandez, Bear, Del.; Mark H. Krackov, West Chester, Pa.

[73] Assignee: E. I. Du Pont de Nemours and Company, Wilmington, Del.

[21] Appl. No.: 831,782

[22] Filed: Feb. 5, 1992

[51] Int. Cl.$^5$ .............................................. C07C 17/20
[52] U.S. Cl. .................................... 568/932; 568/927; 568/937; 568/938; 568/939; 568/940; 570/127; 570/141; 570/144; 570/147; 570/166; 546/345
[58] Field of Search ..................... 546/250, 346, 345; 568/937, 933, 932, 927, 938, 939, 940; 570/127, 141, 143, 144, 182, 190, 225, 147, 166, 161, 164, 170

[56] References Cited

U.S. PATENT DOCUMENTS

| | | | |
|---|---|---|---|
| 3,277,192 | 10/1966 | Crosbie | 570/147 |
| 3,294,629 | 12/1966 | Pyne et al. | 568/937 |
| 3,616,336 | 5/1968 | Childs | 204/140 |
| 4,071,521 | 1/1978 | Muench | 546/345 |
| 4,226,811 | 10/1980 | Oeser et al. | 568/937 |
| 4,568,781 | 2/1986 | Effenberger et al. | 568/937 |
| 4,625,035 | 11/1986 | Werner | 546/345 |
| 4,680,406 | 7/1987 | Fujioka | 570/144 |
| 4,684,734 | 8/1987 | Kaieda et al. | 568/937 |
| 4,973,771 | 11/1990 | Cantrell | 568/937 |
| 4,978,769 | 12/1990 | Kysela et al. | 568/937 |
| 4,990,701 | 2/1991 | Cassel et al. | 570/170 |
| 4,990,702 | 2/1991 | Fernandez et al. | 570/170 |
| 4,999,432 | 3/1991 | Friese et al. | 546/345 |
| 5,073,637 | 12/1991 | Little et al. | 546/345 |

Primary Examiner—Robert L. Stoll
Assistant Examiner—Valerie Fee

[57] ABSTRACT

A process for halogen exchange fluorination or fluorodenitration of aromatic compounds having at least one replaceable non-fluorine halogen or nitro substituent with an anhydrous substantially molten alkali metal acid fluoride composition wherein the alkali metal is potassium, rubidium or cesium.

16 Claims, No Drawings

AROMATIC NUCLEOPHILIC FLUORINATION

FIELD OF THE INVENTION

This invention relates to the preparation of fluorinated aromatic compounds, e.g., benzenoid compounds. It further relates to the preparation of such compounds by nucleophilic replacement of non-fluorine halogen or nitro groups by fluorine.

BACKGROUND OF THE INVENTION

Fluorinated aromatic compounds are known useful starting materials for the manufacture of dyes, pharmaceuticals, agricultural chemicals and polymeric coating materials.

For example, 2-fluoronitrobenzene is an intermediate in the preparation of certain known herbicides; 1,3-difluorobenzene is used to prepare the anti-inflammatory agent "Difunisal" and the insecticide "Dibenzuron"; and 1,2 and 1,4-difluorobenzene are used in the preparation of other pharmaceutically active agents.

Heretofore, fluorinated aromatic compounds have been prepared by reaction of an appropriately substituted aromatic non-fluoro halo- or nitro- compound with an alkali metal fluoride, generally and most advantageously in the presence of an aprotic polar organic solvent. Representative and typical of such solvent-based processes are those disclosed in the following: U.S. Pat. No. 4,069,262 discloses preparing 2-fluoronitrobenzene by reacting 2-chloronitrobenzene with ultra-fine particulate KF in tetramethylenesulfone (sulfolane) containing a macrocyclic ether, i.e., "crown" ether, or a quaternary ammonium halide as catalyst.

U.S. Pat. No. 4,418,229 discloses the production of fluoronitrobenzenes by reacting appropriately substituted chloronitrobenzenes with an alkali metal fluoride at elevated temperatures, in an aprotic, polar organic solvent and a quaternary ammonium salt as phase-transfer catalyst, the quaternary salt being added incrementally during the course of the reaction inasmuch as such catalyst tends to be destroyed at the elevated temperatures employed. The solvents include dimethyl sulfoxide, sulfolane, bis(2-methoxyethyl ether), bis[2-(2-methoxyethoxy)ethyl]ether, hexamethylphosporamide, N-methylpyrrolidinone and dimethylformamide.

U.S. Pat. No. 4,229,365 discloses the preparation of substituted fluorobenzenes bearing nitro or cyano groups, and optionally alkyl or halo groups by reacting an appropriately substituted chlorobenzene with potassium fluoride in the presence of cesium fluoride as catalyst and an N,N-disubstituted carboxylic acid amide, nitrobenzene, nitrile, aliphatic sulfone and/or sulfoxide as the solvent.

U.S. Pat. No. 4,847,442 discloses a multi-step process for preparing 1,3-difluorobenzene which involves (a) halogen exchange fluorination of 2,4- or 2,6-dichlorobenzoyl chloride to the corresponding difluorobenzoyl fluoride by reaction with KF in a solvent in a first step. Solvents employed include amides such as dimethylformamide and N-methylpyrrolidinone, sulfoxides such as dimethyl sulfoxide and sulfones such as sulfolane.

European Patent 354,444/'90A2 discloses the production of fluorinated aromatic compounds by nucleophilic exchange of halo or nitro groups with KF in the presence of a phase transfer catalyst, a salt of a metal of Groups 3 to 5, of the Periodic Table, and preferably a solvent such as "dimethyl sulfoxide, N-methylpyrrolidone, tetramethylsulfone, benzonitrile, nitrobenzene, dimethylacetamide, ethylene glycol dimethyl ether or diglyme".

European Patent Application 0371 563/A2 discloses the preparation of chlorofluoro- and difluorobenzenes in the presence of CsF in a polar aprotic solvent under substantially anhydrous conditions. Suitable aprotic solvents disclosed are N-methylpyrrolidinone, N-cyclohexylpyrrolidinone, 1,3-dimethyl-2-imidazolidinone and 1,3-dimethyl-3,4,5,6-tetrahydro-2-(1H)-pyrimidone.

The prior art processes suffer several disadvantages that add to the cost of assembling and carrying out a viable commercial process. These include the required use of such expedients as: ultra-fine particulate alkali metal fluoride; high-cost ("crown") ethers in an attempt to provide a more reactive "free" fluoride during the course of the reaction; phase-transfer catalysts and the apparent need to control their addition to the reaction medium in view of their tendency to be fugitive at the high temperatures of the halogen exchange replacement reaction; extraneous salt additives, and, most importantly, an aprotic polar solvent medium for the reaction, a requirement common to substantially all the art.

Not only are such solvents relatively expensive, but their use requires facilities for storing, transporting, handling, recovering and purifying them, as well as for preventing their escape into and contaminating the environment. All these expedients add significantly to the investment and operating costs for any process requiring their use.

It is well-known in the art [see, for example, Zoltewicz, Top. Curr. Chem. 59, 33–64 (1975) and Bunnett and Zahler, Chem. Revs. 49, 273–412 (1951)] that nucleophilic exchange in aromatic systems normally requires that the aromatic ring be activated by the presence of an appropriately positioned electron-withdrawing substituent. An important advantage of this invention is that ring activation is not required for substitution to occur.

It is also known, as disclosed by Brown, et al., *Journal of Fluorine Chemistry*, 30, 251–258 (1985), that tetraphenylphosphonium hydrogen difluoride, $(C_6H_5)_4PHF_2$, can fluorinate organic substrates via halogen exchange or fluorodenitration reactions in the presence or absence of solvents. The phosphonium compound, however, suffer the disadvantage that it is much too expensive for commercial use.

OBJECTS OF THE INVENTION

The object of this invention is to provide a nucleophilic replacement/exchange process for the production of fluorinated aromatic compounds which does not require the use of added aprotic polar or other solvents or ultra-fine particulate alkali metal fluoride, or phase transfer—or other catalysts for the reaction.

Another object is to provide such process for the halogen exchange fluorination of aromatic compounds bearing a replaceable non-fluorine halogen substituent or a replaceable nitro substituent.

It is a particular object to provide a simplified process for the halogen exchange conversion of chlorinated benzenes having one or more chlorine substituents to fluorinated benzenes having one or more fluorine substituents, in particular the conversion of 1,3-dichlorobenzene to 1,3-difluorobenzene.

SUMMARY OF THE INVENTION

The objects are accomplished by a nucleophilic replacement process which comprises (1) reacting an aromatic compound having at least one replaceable non-fluorine halogen or nitro substituent with an anhydrous molten alkali metal acid fluoride composition at a temperature and pressure effective to result in the formation of at least one fluorinated aromatic compound having at least one more fluorine substituent than the starting material and (2) isolating and recovering the fluorinated aromatic compound from the residual molten composition.

The process is preferably carried out in the absence of an added solvent other than the organic starting material.

In one aspect of the invention, the nucleophilic replacement process is a halogen exchange process wherein a fluorine group, i.e., a fluoride group of the alkali metal acid fluoride, replaces a non-fluorine halogen, i.e., halide or halo group, from a carbon atom of the aromatic nucleus.

In another aspect, the nucleophilic replacement process is a fluorodenitration, i.e., a fluoride group replaces a nitro group from a carbon atom of the aromatic nucleus.

A preferred embodiment of the invention comprises a halogen exchange process for the preparation of 1,3-difluorobenzene by reaction of 1,3-dichlorobenzene and/or 1-chloro-3-fluorobenzene with an effective substantially molten alkali metal acid fluoride composition.

By an effective molten alkali metal acid fluoride composition is meant that the alkali metal fluoride is chemically combined with hydrogen fluoride (HF) in an amount sufficiently large to form a composition that is substantially molten at the replacement temperature and pressure but is not so large as to render the composition unable to effect the replacement reaction.

The alkali metal acid fluoride composition normally contains at least 50 mole percent, preferably at least 80 mole percent, of a compound having the formula MF.nHF, wherein "M" is at least one of potassium, K, rubidium, Rb, and cesium, Cs, preferably Cs, and "n" is a number of from about 0.5 to 2, preferably 0.5 to 1, more preferably 0.5 to 0.9.

The invention process is inherently protic since it employs alkali metal acid fluorides as reaction medium as well as reactant. It also makes unnecessary the use of such expedients as aprotic or other solvents, ultra-fine particulate alkali metal fluorides, ethers, quaternary ammonium compounds and extraneous metal salts as catalysts, which characterize the processes of the prior art.

DETAILED DESCRIPTION OF THE INVENTION

In general, the invented process is conducted by initially contacting by vigorously agitating, batchwise or continuously, the aromatic starting material with an alkali metal acid fluoride composition at an effective temperature and pressure for a time sufficient to result in the formation of at least one fluorinated product having at least one more fluorine in the molecule than the starting material; and separating the fluorinated reaction product from the residual, at least partially spent (i.e., at least partially depleted fluoride content) alkali metal composition. The invention is applicable to the fluorination of aromatic compounds, which may be benzenoid or pyridinoid, having one or more replaceable non-fluorine halogen or nitro groups; halo substituents are normally chloro or bromo, with chloro preferred for reasons of economy.

More specifically, the aromatic starting materials can be represented by the formula:

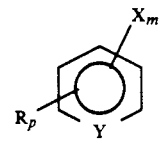

where X is non-fluorine halo and/or nitro, m is 1 to 6, R is hydrogen, hydrocarbyl, halogenated hydrocarbyl, amino ($NH_2$), cyano (CN) and/or carbonylhalide (COZ), Y is CH or N, p is 0 to 5 and m+p is 1 to 6. The hydrocarbyl groups may be aryl or alkyl, preferably alkyl, more particularly methyl; the halogenated hydrocarbyl groups are preferably halogenated alkyl, more preferably especially trifluoromethyl. The carbonyl halide group is preferably the chloride (Z=Cl) or fluoride (Z=F).

In a preferred situation the aromatic starting material is benzenoid (Y=CH), X is chloro and/or nitro, R is hydrogen, fluoro, methyl, trifluoromethyl, amino and/or cyano, m is 1 to 3, p is 0 to 5 and p+m is 1 to 6.

Representative aromatic starting materials and their products of halogen exchange or fluorodenitration are tabulated below.

| Starting Materials | Halogen Exchange Product |
|---|---|
| chlorobenzene | fluorobenzene |
| ortho-dichlorobenzene | 1-chloro-2-fluorobenzene |
| 1-chloro-2-fluorobenzene | 1,2-difluorobenzene |
| meta-dichlorobenzene | 1-chloro-3-fluorobenzene |
| 1-chloro-3-fluorobenzene | 1,3-difluorobenzene |
| para-dichlorobenzene | 1-chloro-4-fluorobenzene |
| 1-chloro-4-fluorobenzene | 1,4-difluorobenzene |
| 1,2,4-trichlorobenzene | mixture including $C_6H_3Cl_2F$, $C_6H_3ClF_2$ and 1,2,4-trifluorobenzene |
| 3-chlorotoluene | 3-fluorotoluene |
| hexachlorobenzene | mixture including $C_6Cl_5F$ and $C_6Cl_3F_3$, $C_6Cl_2F_4$, $C_6Cl_5F$ |
| 3-chlorobenzotrifluoride | 3-fluorobenzotrifluoride |
| 4-chlorobenzotrifluoride | 4-fluorobenzotrifluoride |
| 3,4-dichlorobenzotrifluoride | monochloro-monofluorobenzotrifluoride |
| 3,4,5-trichlorobenzotrifluoride | monofluoro-dichlorobenzotrifluoride |
| 2-chloronitrobenzene | 2-fluoronitrobenzene |
| 3-chloronitrobenzene | 3-fluoronitrobenzene |

| Starting Materials | |
| --- | --- |
| 2,4-dichloro-5-fluoronitrobenzene | 2,4,5-trifluoronitrobenzene |
| 2,6-dichlorobenzonitrile | 2-chloro-6-fluorobenzonitrile |
| 2-chloro-6-fluorobenzonitrile | 2,6-difluorobenzonitrile |
| 2,4-dichlorobenzoylchloride | 2,4-difluorobenzoylfluoride |
| 3-chloroaniline | 3-fluoroaniline |
| 3-chloropyridine | 3-fluoropyridine |
| 2-chloro-5-nitropyridine | 2-fluoro-5-nitropyridine |
| pentafluoropyridine | mono-, di and trifluoropyridines |
| 2,4-dichlorobiphenyl | 2,4-difluorobiphenyl |
| | Fluorodenitration Product |
| 4-nitrobenzotrifluoride | 4-fluorobenzotrifluoride |
| 1,2-dinitrobenzene | 2-fluoronitrobenzene |
| 1,4-dinitrobenzene | 4-fluoronitrobenzene |
| 2-nitrobenzonitrile | 2-chloro-6-fluorobenzonitrile |
| 2,3,5,6-tetrachloronitrobenzene | mixed 2,3,5,6-tetrachlorofluorobenzene |
| pentachloronitrobenzene | mixed pentachloro-fluorobenzenes |

In a particularly preferred embodiment, the aromatic starting material is 1,3-dichlorobenzene or 1-chloro-3-fluorobenzene and the product is 1,3-difluorobenzene.

The alkali metal acid fluorides are well-known compositions and can be represented as MF.nHF, where M stands for at least one alkali metal and n is a number of from about 0.5 to 1, preferably 0.6 to 0.9.

The alkali metal is preferably potassium (K), rubidium (Rb) or cesium (Cs), more preferably Cs. Any of the other alkali metals and/or compatible metals (alkaline earth or aluminum) may be present in minor amounts. The alkali metal acid fluoride is employed in the substantially anhydrous molten state. In general, the higher the value of n (in MF.nHF) and the greater the atomic weight of the alkali metal, the lower is the melting point of the alkali metal acid fluoride. Preferably, the acid fluoride will be so constituted as to be substantially molten below about 250° C. and more preferably, below about 225° C. The melting points of the alkali metal fluorides and various acid fluorides are given in U.S. Pat. Nos. 4,990,701 and 4,990,702 and are incorporated herein by reference. The acid fluoride composition may also contain alkali metal halides other than the fluorides. These can vary widely as to the metal, the halide and their amounts provided that the resulting alkali metal composition contains sufficient hydrogen and fluoride ions that the composition corresponds empirically to at least 50 mole percent of MF.nHF as defined above and is substantially molten during the course of the reaction.

By substantially molten is meant that the alkali metal acid fluoride composition in the molten state may contain insoluble matter, such as metal salt by-products of halogen exchange reactions, so long as the liquid phase contains alkali metal acid fluoride and is stirrable.

The relative proportions of the alkali metal acid fluoride and the starting material can vary widely, from about 1 to 99 mole percent to 99 to 1 mole percent. The acid fluoride is preferably used in excess so as to serve as molten reaction medium as well as reactant, with molar ratios of acid fluoride to aromatic starting material generally in the range of about 10:1 to 50:1.

If necessary, the value of "n" and the molten character of the acid fluoride composition can be maintained at an effective level by the addition of additional alkali metal fluoride or HF as needed during the course of the reaction.

The fluorination temperatures can vary widely provided that they are sufficiently high to maintain the acid fluoride composition in a substantially molten condition, but not so high as to result in decomposition of the aromatic reactant or the fluorination products. The reaction temperatures will normally be within a range of from about 200° to 400° C., depending upon the particular reactant, the fluorinated products and the melting characteristics of the alkali metal acid fluoride-based composition. Preferably the temperature will be within the 250° to 375° C. range, more preferably within the 300° to 350° C. range.

Reaction pressure is not critical. It may vary from subatmospheric to superatmospheric, but preferably the pressure is at least atmospheric. Superatmospheric pressures, up to about 30 atmospheres, may be preferred to the extent that the solubility of the aromatic reactant in the molten acid fluoride increases with the increased pressure and results in increased reaction rate and/or conversion to the fluorocarbon product.

Reaction time may also vary widely depending on the nature of the starting material, the alkali metal acid fluoride and the result desired. In general, it will be in the range of 1 to 30 hours.

The process is conveniently conducted batchwise by mixing the reactants in a closed or ventible system and heating the mixture under agitation at a desired temperature and pressure, the pressure being controlled with a pressure-relief valve. The process can also be conducted continuously or semi-continuously with the aromatic starting material fed, with or without HF, to the reactor containing the alkali metal acid fluoride continuously or intermittently, and with the organic reaction product taken off continuously or intermittently. Where the organic reaction products are gaseous over the operating temperatures and pressures, it is convenient to bleed off a portion of the vapor phase intermittently or continuously during the course of the reaction.

The product mixture can be resolved into its components by any of a variety of well-known techniques, including extraction, distillation and crystallization from solvents. Unreacted and incompletely fluorinated material can be recycled to the reactor for fluorination.

The reaction vessel is constructed of materials resistant to the action of the reactants. Examples of such materials include stainless steels, high nickel alloys such as "Hastelloy" and Inconel", and plastics such as polyethylene, polychlorotrifluoroethylene, and polytetrafluoroethylene.

In the following examples, the product mixtures were analyzed by gas chromatography (GC) and mass spectroscopy (MS). The reactor employed was equipped with an agitator, temperature controller and a back-pressure regulator to enable control of the reaction pressure and to allow sampling of the organic reaction products during the course of the reaction.

Specific embodiments of the invention are illustrated in the examples which follow: The procedure of Example 3 is the best mode contemplated for performing the invention.

The examples were conducted in a 600 ml Parr autoclave composed of stainless steel, "Inconel" alloy or "Hastelloy". The autoclave was equipped with a gas feed tube, an outlet tube, a stirrer, a heating mantle controlled by a thermocouple centered within the reactor and a pressure transducer for monitoring pressure within the autoclave. The outlet tube was connected to a system of three scrubbers in series. The first two of these contained equal volumes of 20% aqueous sodium hydroxides and an appropriate organic solvent, the third only aqueous caustic. The organic layers were separated and analyzed by GC. Alternatively, the gaseous effluent from the reactor was fed through an aqueous scrubber system and them directly to a GC adapted to automatically sample and analyze the gas stream. In some examples, the GC results were confirmed with a mass spectrometer (MS). All reactants employed were anhydrous. The gas chromatograph (GC) was a "Hewlett Packard" 5880 model utilizing a flame ionization detector and a customized 4-component column. Analyses of the aqueous scrubber solution(s) were carried out using fluoride and chloride specific ion electrodes.

EXAMPLE 1

To a Hastelloy C Parr reactor was added 759.5 g (5 moles) CsF, 90.0 g (4.5 moles) HF and 56.3 g (0.5 mole) chlorobenzene. The reactor was sealed, heated to 200° C. under autogenous pressure and held for 24 hours under agitation. Samples taken during this period and analyzed chromatographically showed only trace amounts of fluorobenzene being formed.

The temperature was raised to 300° C. over a 3-hour period and maintained at that temperature for 30 hours. The fluorobenzene increased to 6.1% and the chlorobenzene percent decreased to 93.8%.

EXAMPLE 2

The procedure of Example 1 was repeated except the reactor and the reaction mass were heated directly to 300° C. and an autogeneous pressure of about 315 psig in 0.67 hour. Samples taken periodically were drowned on crushed ice; the organic layer removed and analyzed. After 10 hours of reaction time the fluorobenzene content of the samples reached a maximum of 10.5 percent in 10 hours, but decreased to 7.9% after an additional hour.

EXAMPLE 3

To a Hastelloy C Parr autoclave (600 ml) fitted with a variable speed agitator and thermostatically controlled heater was added 758.8 g (5.0 moles) of cesium fluoride (CsF). The reactor was sealed and all oxygen removed by alternately evacuating the reactor and refilling with nitrogen. After a final evacuation, 80 g (4.0 moles) of anhydrous HF was sucked into the reactor, and the reactor was allowed to warm until the mixture was molten.

To the reaction mass was now charged 10.0 g (0.068 mole) of m-di-chlorobenzene (m-DCB). The reactor was rapidly heated to 350° C. and the mass held at that temperature for 5.63 hours, while being agitated at a rate of 1600 rpm. Temperature and pressure were monitored throughout the run. At the end of this time, the agitation rate was reduced to 600 rpm and the exit valve opened to allow the volatile organic products to exit the reactor. These were collected in a toluene scrubber and analyzed by gas chromatography, using an internal standard method. Conversion of the m-DCB was 96.9%. Products, with yield (based on starting material consumed) in parentheses, were as follows: m-difluorobenzene (95%), p-difluorobenzene (1.36%), o-difluorobenzene (3.18%), m-chlorofluorobenzene (1.82%). Traces of p-chlorofluorobenzene, o-chlorofluorobenzene and chlorobenzene were also found. Mass balance was 101%. The molten salt remaining in the reactor may be used for several runs.

EXAMPLE 4

To the Parr reactor was added 760 g (5 moles) CsF. The reactor was sealed, evacuated, and purged twice with dry $N_2$ gas. The reactor was again evacuated and 21.31 g (0.118 mole) 3-chlorobenzotrifluoride and 80 g (4 moles) HF were added at room temperature. The sealed reactor was then heated to 300° C. with stirring (1700 rpm) and held at this temperature for 1 hour.

The stirrer speed was then reduced to 400 rpm and the reactor was vented to a scrubber system comprising three scrubbers in series. The first two scrubbers each contained 100 cc of 20% NaOH and 100 cc toluene, the third scrubber only aqueous caustic. Once the reactor was substantially completely vented, its vapor space was purged with $N_2$ for 2.5 hours, the purge stream passing through the scrubbers.

The toluene layers of the first two scrubbers were isolated and the aqueous layer of each scrubber was washed with 50 cc toluene. The reaction mass remaining in the reactor was dissolved in 200 cc of 20% NaOH and the solution extracted with 200 cc toluene. The toluene solutions were analyzed for 3-chlorobenzotrifluoride and 3-fluorobenzotrifluoride with the following results: conversion of the 3-chloro- to the 3-fluoro compound in the 1 hour of reaction time was 21.1%; yield of the 3-fluorobenzotrifluoride based on the 3-chlorobenzotrifluoride converted was 14.1%.

EXAMPLE 5

The procedure of Example 4 was repeated with 4-chlorobenzotrifluoride in place of the 3-chloroisomer. The conversion after 1 hour was 31.6%, the yield of the 4-fluoro product was 43.2% based on the amount of the starting material converted.

EXAMPLE 6

Repeating Example 5 for 4-hours resulted in a 67% conversion of the 4-chloro compound and a 77% yield on conversion of the 4-fluorobenzotrifluoride.

EXAMPLE 7

The procedure of Example 4 was repeated except that 3-chloroaniline (15 g, 0.118 mole) was employed as starting material. Analysis of the toluene extracts showed the reaction product consisted of 2-fluoroaniline (2.2% of theory), 3-fluoroaniline (11.8% of theory) and 4-fluoroaniline (0.17% of theory). 5.13% of the 3-chloroaniline was recovered.

The 2- and 4-isomers evidently result from isomerization occurring during the course of the reaction. The degree of isomerization and the extent of decomposition of starting material/products may be lowered by operating at lower temperatures and/or shorter reaction times in corrosion resistant equipment.

EXAMPLE 8

The procedure of Example 4 was followed using 3-chloropyridine as starting material. The resulting reaction mass was blackened and tarry. 3-Fluoropyridine (2.62% of theory) was found in the scrubbers.

EXAMPLE 9

The procedure of Example 4 was followed except that the starting material was 4-nitrobenzotrifluoride ($O_2N\text{-}C_6H_4\text{-}CF_3$, 5.5 g=0.029 mole) and the reaction temperature was 190° C. The resulting toluene solutions contained 4-nitrobenzotrifluoride (3.68% recovery) and 4-fluorobenzotrifluoride (15.6% based on conversion).

EXAMPLE 10

The procedure of Example 3 was repeated using 87.6 g (0.48 mole) of 1,2,4-trichlorobenzene. After 24 hours at a reactor temperature of 350° C., 99.7% of the starting material was converted. Product yields were as follows: 1,2,4-trifluorobenzene (22.1%), mixed difluorochlorobenzenes (50.2%), mixed dichlorofluorobenzenes (2.7%). The overall material balance was 87%.

EXAMPLE 11

The procedure of Example 1 was used except that the starting material was 3-chlorotoluene, the temperature was 350° C. and the reaction time was 5 hours. 3-fluorotoluene was produced in a 39% yield.

EXAMPLE 12

The procedure of Example 1 was followed except that the starting material was 3-chloro-nitrobenzene, the temperature was 200° C. and the reaction time 5 hours. 3-Fluoronitrobenzene was detected in the reaction mixture.

The 3-fluoronitrobenzene yield may be increased by operating for longer reaction times.

EXAMPLE 13

Example 3 was repeated with o-dichlorobenzene (o-DCB) in place of m-DCB and at a reaction temperature of 325° C. After a reaction time of 5.63 hours, the o-DCB conversion was 84.5%. Product yields, based on starting material converted, were as follows: o-difluorobenzene (34.4%), m-difluorobenzene (2.8%), p-difluorobenzene (3.5%), o-chlorofluorobenzene (48.6%), p-chlorofluorobenzene (7.0%). Other products formed in small amounts were m-chlorofluorobenzene, p-dichlorobenzene and chlorobenzene. The mass balance was 93%.

We claim:

1. A process for the nucleophilic fluorination of a starting compound having at least one replaceable non-fluorine halogen or nitro substituent on at least one aromatic ring having the structure

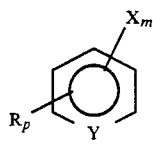

where
X is non-fluorine halo and/or nitro
m is 1 to 6, R is hydrogen, hydrocarbyl, halogenated hydrocarbyl, amino, cyano and/or carbonylhalide,
Y is CH or N, p is 0 to 5 and m+p is 1 to 6,
to a compound having at least one more fluorine in the molecule than the starting compound which comprises the following steps: (1) intimately contacting the starting compound with an anhydrous molten composition containing at least 50 mole % of a compound or compounds having the formula MF.nHF wherein "M" is at least one of potassium, cesium, or rubidium, HF is hydrogen fluoride and "n" is a number from about 0.5 to about 2, at a temperature within the range of about 30° C. up to a temperature below the decomposition temperature of said starting compound or said fluorinated compound, whichever is lower, at a pressure and for a time sufficient to yield at least one reaction product wherein at least one fluorine has replaced at least one non-fluorine halogen or nitro substituent of said starting compound and a residual molten composition and (2) isolating and recovering the fluorinated reaction product from the residual molten composition.

2. A process as in claim 1 wherein "M" is cesium.

3. A process as in claim 1 wherein "n" is 0.5–0.9.

4. A process as in claim 1 wherein said starting compound is 1-chloro-3-fluorobenzene and said fluorinated compound is 1,3-difluorobenzene.

5. A process as in claim 1 wherein said starting compound is 1,3-dichlorobenzene, and said fluorinated compound is 1,3-difluorobenzene.

6. A process as in claim 1 wherein said starting compound is 3-chlorobenzotrifluoride and said fluorinated product is 3-fluorobenzotrifluoride.

7. A process as in claim 1 wherein said starting compound is 4-chlorobenzotrifluoride and said fluorinated product is 4-fluorobenzotrifluoride.

8. A process as in claim 1 wherein said starting compound is 3-chloroaniline and said fluorinated product is 3-fluoroaniline.

9. A process as in claim 1 wherein said starting compound is 3-chloropyridine and said fluorinated product is 3-fluoro-pyridine.

10. A process as in claim 1 wherein said starting compound is 3-chlorotoluene and said fluorinated product is 3-fluoro-toluene.

11. A process as in claim 1 wherein said starting compound is 3-chloro-nitrobenzene and said fluorinated product is 3-fluoro-nitrobenzene.

12. A process as in claim 1 wherein said starting compound is ortho-dichlorobenzene and said fluorinated product is orthodifluorobenzene.

13. A process as in claim 1 wherein said starting compound is 1,2,4-trichlorobenzene and said fluorinated product is 1,2,4-trifluorobenzene.

14. The process of claim 1 wherein the replacement process is a fluorodenitration process, the starting compound has at least one replaceable nitro group and the resulting fluorinated product has at least one fluoro substituent that has replaced said nitro group of the starting compound.

15. The process of claim 1 wherein the starting compound has at least one replaceable non-fluorine halogen or nitro substituent on at least one aromatic ring wherein Y is CH.

16. The process of claim 1 wherein the starting compound has at least one replaceable non-fluorine halogen or nitro substituent on at least one aromatic ring wherein Y is N.